(12) United States Patent
Macor

(10) Patent No.: US 7,770,817 B2
(45) Date of Patent: Aug. 10, 2010

(54) AIR FRESHENER WITH SCENT(S) OF A NEW CAR

(75) Inventor: Richard J. Macor, Hunterdon County, NJ (US)

(73) Assignee: Proprietary Technologies, Inc., Hunterdon County, NJ (US)

( * ) Notice: Subject to any disclaimer, the term of this patent is extended or adjusted under 35 U.S.C. 154(b) by 139 days.

(21) Appl. No.: 11/716,420

(22) Filed: Mar. 9, 2007

(65) Prior Publication Data

US 2008/0219897 A1 Sep. 11, 2008

(51) Int. Cl.
*A24F 25/00* (2006.01)
(52) U.S. Cl. .............................. 239/34; 239/57; 239/58; 422/123; 206/0.5; 424/84
(58) Field of Classification Search .................. 239/34, 239/57, 58, 59; 422/123; 206/0.5; 424/84
See application file for complete search history.

(56) References Cited

U.S. PATENT DOCUMENTS

| | | | | |
|---|---|---|---|---|
| 2,738,224 | A * | 3/1956 | Turner et al. | 239/57 |
| 4,905,898 | A * | 3/1990 | Wade | 239/57 |
| 5,478,505 | A * | 12/1995 | McElfresh et al. | 239/57 |
| 6,340,120 | B1 * | 1/2002 | Seymour | 239/34 |
| 7,111,794 | B2 * | 9/2006 | Timpson | 239/34 |
| 2008/0295457 | A1 * | 12/2008 | Kaniecki et al. | 53/428 |

* cited by examiner

*Primary Examiner*—Steven J Ganey

(57) ABSTRACT

In one embodiment, the present invention is a portable air scenting device which comprises at least one material used in the manufacture of an interior part of a new transportation vehicle such as an automobile. The material has at least one scent, and the material is prepared and formed to have an enhanced surface exposure to enhance the at least one scent of the material.

19 Claims, 1 Drawing Sheet

AIR FRESHENER WITH SCENT(S) OF A NEW CAR

FIELD OF THE INVENTION

The present invention relates to air fresheners, particularly portable devices for use in transportation vehicles such as automobiles, trucks, etc.

BACKGROUND OF THE INVENTION

Air freshener (or scenting) devices have been around for many years to provide a predetermined scent to an environment such as a house room, car, truck, etc. The air freshening devices for house rooms, cars, trucks etc. often use a chemical in a solid or liquid form to provide a predetermined, pleasant scent or scents and/or to mask unpleasant odors in an environment. For example, most air fresheners made for a transportation vehicle such as a car, truck, etc. are simply small hanging pieces of cardboard that usually have a predetermined shape, design, color and scent.

Applicant believes that most people like the smell or scent(s) of a new transportation vehicle such as a new car, however, the pleasant new car scent(s) usually wear out and expire after a few months as the new vehicle becomes older. Accordingly, applicant contemplates an air scenting device that can, for example, provide the scent(s) of a new car, for use in an older car that has lost its desirable, new car scent(s).

SUMMARY OF THE INVENTION

In one embodiment, the present invention is a portable air scenting device which comprises at least one material used in the manufacture of an interior part of a new transportation vehicle such as an automobile. The material has at least one scent, and the material is prepared and formed to have enhanced surface exposure to enhance the at least one scent of the material.

Applicant considers the following objectives for the present invention.

It is an important objective of the present invention air freshener device that it can effectively provide the scent(s) of a new transportation vehicle such as a new car, for use in an older car that has lost its new car scent(s).

It is another important objective of the present invention that it be relatively small so that it may be stored inconspicuously, for example, under the seat of a car, etc.

It is another objective of the present invention that it be manufactured (if and when possible) using scrap materials from new car manufacturers, whereby interior material scraps that would be otherwise wasted and disposed, are recycled into the present invention.

And, it is another objective of the present invention that it be cost efficient to manufacture and commercially viable.

DETAILED DESCRIPTION OF THE DRAWINGS

The various drawings provided herein are for the purpose of illustrating possible embodiments of the present invention and not for the purpose of limiting same. Therefore, the drawings herein represent only a few of the many possible embodiments, variations and/or applications of the present invention.

Figure 1:
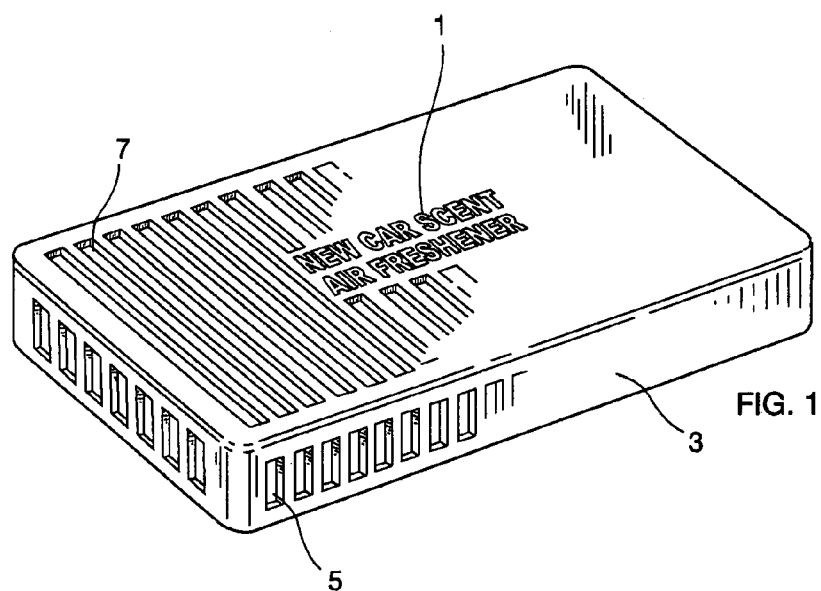
FIG. 1 shows a perspective view of an embodiment of the present invention air freshener device.
Figure 2:
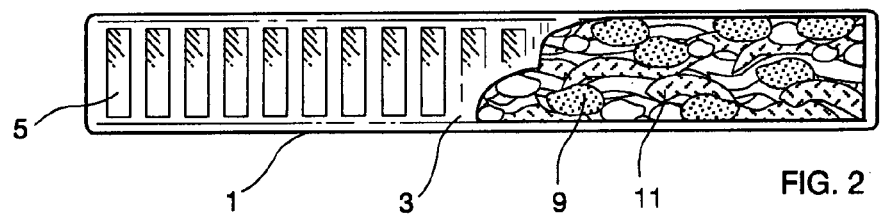
FIG. 2 shows front elevation, cut view of the air freshener device shown in FIG. 1.

Referring to FIGS. 1 and 2 together, FIG. 1 shows a perspective view of a possible embodiment of the present invention air freshener device, and FIG. 2 shows a front elevation, cut view of the air freshener device shown in FIG. 1. In this embodiment of the present invention shown, a portable air scenting device 1 has an outer housing 3 with cut-out top and side vents 7 and 5 respectively. Outer housing 3 is molded from a material the same or similar to the plastic material used in the interior door panels of a new transportation vehicle such as a car. The cut out vents which cover the top and all side surfaces provide two purposes. First, the cut-out vents provide enhanced surface exposure of the plastic material used to form the housing so that the plastic scent(s) of the housing are enhanced more than if the plastic housing had not been prepared and formed with the enhanced surface exposure of the cut out vents. And second, the vents provide an outlet for the scent(s) of the materials placed inside housing 3 to vent, such as shredded leather scraps 11 and vinyl pellets 9 as shown. By shredding a piece of leather applicant believes the scents(s) of the leather are enhanced more so than if the leather had not been shredded. The word "enhanced" shall be defined herein as "to heighten, increase or make greater." A "shredded" material shall be defined herein as a material that has been cut or torn into smaller pieces from a larger piece of material. It's not necessary that the leather be shredded, but preferred embodiments of the present invention comprise material(s) that are prepared and formed having enhanced surface exposure, and cutting or tearing the leather into smaller pieces in one way of achieving that objective. There are many ways to increase the surface exposure of a material which may include methods such as cutting, surface cutting, shredding, grinding, hole punching, palletizing etc. For example, the vinyl pellets such as pellet 9 in housing 3 are prepared and formed as a small pellet to enhance surface exposure of the material in order to enhance the scent(s) of the vinyl material. A "pellet" shall be defined herein as a small material mass of any shape.

Therefore, the present invention comprises at least one material used in the manufacture of an interior part of a new transportation vehicle such as an automobile, which is then prepared and formed with enhanced surface exposure to enhance the inherent scent of the material. In the embodiment shown here in FIGS. 1 and 2, there are three materials used including vented plastic housing 3, shredded leather scraps 11, and vinyl pellets 9. These materials need not be the "actual" materials used in the manufacture of a new transportation vehicle such as an automobile, but may simply be a similar or equivalent material providing similar or equivalent scent(s). Therefore, "material" shall be broadly defined herein as "any matter that may be generally classified by its composition" such as leather, plastic, vinyl, carpeting, fabric, foam, metal etc. to name a few. In some preferred embodiments of the present invention, applicant contemplates utilizing actual scraps from new transportation vehicle manufacturers, to provide material for the present invention while minimizing material waste. In fact, new transportation vehicle manufacturers could custom develop air scenting devices utilizing the actual material scraps they would otherwise discard, and then sell the air scenting devices to their customers through their customer service networks and/or dealerships providing a mutual benefit to both manufacturer and customer. Since the scent(s) of the materials used in the present invention would be subject to expiration, applicant contemplates embodiments of the present invention being freshly packaged in an airtight plastic bag, package or storage device to preserve the scent(s) of the material(s), until the air scenting device is utilized. For example, someone with an older car might buy a present invention air freshener device 1, remove it from an airtight storage bag (not shown), and place it under the seat of an older car to temporarily provide the older car with the fresh scent(s) of a new car.

Figure 3:
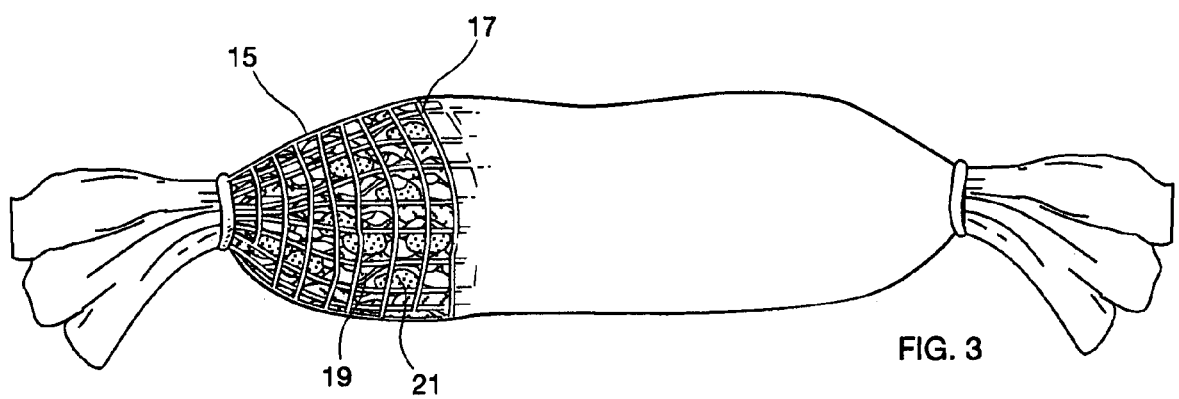
FIG. 3 shows a perspective view of another embodiment of the present invention air freshener device.

FIG. 3 shows a perspective view of another possible embodiment of the present invention air freshener device, wherein air scenting device 15 has a porous vinyl bag 17 that contains cut seat fabric scraps such as fabric scrap 17 and plastic pellets such as plastic pellet 21. The combination of these three fresh materials, for example, may provide the scents of a new car having fabric covered seats.

Upon reading and understanding the specification of the present invention described above, modifications and alterations will become apparent to those skilled in the art. It is intended that all such modifications and alterations be included insofar as they come within the scope of the patent as claimed or the equivalence thereof.

Having thus described the invention, the following is claimed:

1. A portable air scenting device comprising at least two different materials each used in the manufacture of an interior part of a new transportation vehicle, each of said at least two materials having at least one scent, and, at least one of said at least two materials being prepared and formed having enhanced surface exposure so as to enhance the at least one scent of the at least one of said at least two different materials.

2. A portable air scenting device of claim 1, wherein at least one of said at least two materials is in a shredded like form.

3. A portable air scenting device of claim 1, wherein at least of said at least two materials is in a pellet like form.

4. A portable air scenting device of claim 1, wherein at least one of said at least two materials is a synthetically produced compound such as a plastic like material.

5. A portable air scenting device of claim 1, wherein at least one of said at least two materials is a leather like material.

6. A portable air scenting device of claim 1, wherein at least one of said at least two materials is a carpeting like material.

7. A portable air scenting device of claim 1, wherein said air scenting device is packaged in a substantially airtight storage device to preserve the scents of the at least two different materials, until the air scenting device is utilized.

8. A portable air scenting device of claim 1, wherein said device comprises a housing, and said housing comprises at least one of said at least two materials.

9. A portable air scenting device of claim 1, wherein said device comprises a bag, and said bag comprises at least one of said at least two materials.

10. A portable air scenting device comprising at least two different materials each used in the manufacture of an interior part of a new transportation vehicle and, each of said at least two different materials having at least one scent.

11. A portable air scenting device of claim 10, wherein at least one of said at least two different materials is in a shredded like form.

12. A portable air scenting device of claim 10, wherein at least one of said at least two different materials is in a pellet like form.

13. A portable air scenting device of claim 10, wherein at least one of said at least two different materials is a synthetically produced compound such as a plastic like material.

14. A portable air scenting device of claim 10, wherein at least one of said at least two different materials is a leather like material.

15. A portable air scenting device of claim 10, wherein said air scenting device is packaged in a substantially airtight storage device to preserve the scents of the at least two different materials, until the air scenting device is utilized.

16. A portable air scenting device comprising at least one material used in the manufacture of an interior part of a new transportation vehicle, said at least one material having at least one scent, and, said at least one material being a leather like material.

17. A portable air scenting device of claim 16, wherein said at least one material is formed having enhanced surface exposure so as to enhance the at least one scent of the at least one material.

18. A portable air scenting device comprising at least one material used in the manufacture of an interior part of a new transportation vehicle, said at least one material having at least one scent, and, said at least one material being a carpeting like material.

19. A portable air scenting device of claim 18, wherein said at least one material is formed having enhanced surface exposure so as to enhance the at least one scent of the at least one material.

\* \* \* \* \*